US012584899B2

(12) United States Patent     (10) Patent No.:   US 12,584,899 B2

Juhl et al.     (45) Date of Patent:    Mar. 24, 2026

---

(54) METHOD OF AND ANALYSER FOR THE OPTICAL ANALYSIS OF A LIQUID CONTAINING A DISSOLVED GAS

(71) Applicant: Foss Analytical A/S, Hilleroed (DK)

(72) Inventors: Henrik Vilstrup Juhl, Hilleroed (DK); Hans Villemoes Andersen, Hilleroed (DK)

(73) Assignee: FOSS Analytical A/S, Hilleroed (DK)

( * ) Notice: Subject to any disclaimer, the term of this patent is extended or adjusted under 35 U.S.C. 154(b) by 269 days.

(21) Appl. No.: 18/249,652

(22) PCT Filed: Sep. 30, 2021

(86) PCT No.: PCT/IB2021/058978

§ 371 (c)(1),
(2) Date: Apr. 19, 2023

(87) PCT Pub. No.: WO2022/090832

PCT Pub. Date: May 5, 2022

(65) Prior Publication Data

US 2023/0393112 A1     Dec. 7, 2023

(30) Foreign Application Priority Data

Nov. 2, 2020    (DK) .............................. PA202001232

(51) Int. Cl.
    *G01N 33/14*       (2006.01)
    *G01N 21/31*       (2006.01)
    *G01N 21/85*       (2006.01)

(52) U.S. Cl.
    CPC ........... *G01N 33/146* (2013.01); *G01N 21/31* (2013.01); *G01N 21/85* (2013.01); *G01N 2021/8571* (2013.01)

(58) Field of Classification Search
CPC ...... G01N 33/146; G01N 21/31; G01N 21/85; G01N 2021/8571; G01N 2021/054; G01N 2201/129
See application file for complete search history.

(56) References Cited

U.S. PATENT DOCUMENTS

| | | | |
|---|---|---|---|
| 2007/0048183 A1 | 3/2007 | Nguyen et al. | |
| 2013/0156646 A1* | 6/2013 | Bernhard ........... | B01D 19/0036 96/201 |

(Continued)

FOREIGN PATENT DOCUMENTS

| | | |
|---|---|---|
| DE | 10352924 A1 | 7/2005 |
| EP | 2739635 A1 | 6/2014 |

(Continued)

OTHER PUBLICATIONS

International Search Report PCT/ISA/210 for International Application No. PCT/IB2021/058978 on Nov. 29, 2021.

(Continued)

*Primary Examiner* — Timothy P Graves
(74) *Attorney, Agent, or Firm* — Harness, Dickey & Pierce, P.L.C.

(57)        ABSTRACT

A method of performing an optical analysis of a liquid containing dissolved gas includes transferring an amount of the liquid containing the dissolved gas from a reservoir into a holder of a flow system of the optical analyser, holding the amount of the liquid in the holder at around ambient pressure for a period such that a portion of the dissolved gas is expelled from the amount of liquid held in the holder while the holder is open to a waste reservoir, transferring at least a portion of the amount of the liquid containing the dissolved gas held in the holder under a pressure above ambient into a measurement cell of the optical analyser as a liquid sample, and performing the optical analysis of the liquid (Continued)

Transfer from Reservoir to Cylinder of Piston Pump   — A

Hold in Cylinder for Partial Degassing   — B

Transfer Liquid Sample from Cylinder to Measurement Cell under Back Pressure   — C Perform Optical Analysis of Liquid Sample   — D sample from a detection of optical radiation by an optical detector after its interaction with the liquid sample in the measurement cell.

15 Claims, 3 Drawing Sheets

(56) References Cited

U.S. PATENT DOCUMENTS

2017/0285057 A1 * 10/2017 Andersen ............... G01N 21/05
2019/0301981 A1 * 10/2019 Seidel ................. G01N 1/2035

FOREIGN PATENT DOCUMENTS

WO        WO-98/20338 A1     5/1998
WO     WO-2019/093907 A1     5/2019

OTHER PUBLICATIONS

Written Opinion PCT/ISA/237 for International Application No. PCT/IB2021/058978 on Nov. 29, 2021.
Danish Search Report for DK Application No. PA202001232 on Jan. 29, 2021.

* cited by examiner

METHOD OF AND ANALYSER FOR THE OPTICAL ANALYSIS OF A LIQUID CONTAINING A DISSOLVED GAS

CROSS-REFERENCE TO RELATED APPLICATIONS

This application is a National Stage of PCT/162021/058978, filed on Sep. 30, 2021, which claims priority to Danish Patent Application PA202001232, filed on Nov. 2, 2020 in the Danish Patent and Trademark Office, the entire contents of each of which are incorporated herein in their entirety.

BACKGROUND

The present invention relates to the optical analysis of a liquid containing a dissolved gas, and in particular to optical analysis by optical spectroscopy.

It is well known to determine components of a liquid sample using optical spectroscopy measurements in an optical analyser. The liquid sample is interrogated by transmitting optical radiation from a light source, configured to generate optical radiation selected from within the wavelength region from and including the ultra-violet to and including the infrared, into the liquid sample and measuring a wavelength dependent attenuation of the interrogating optical radiation caused by constituents of the liquid sample. Measurements are typically made using a spectrometer, such as an interferometer or a monochromator. From these measurements, components of interest within the liquid sample are identified and optionally their concentrations are calculated using a data processor and standard chemometric techniques. The identification and/or calculation is performed in the data processor which is adapted to apply a calibration or predictive model, by which is established a relationship between the component of interest and measured wavelength dependent attenuation of the optical radiation, to the wavelength dependent attenuation of the optical radiation measured by the spectrometer.

An optical analyser for this purpose generally comprises a measurement cell for receiving therein a liquid sample, the measurement cell being configured to permit interaction of optical radiation with the liquid sample inside the cell; a source configured to generate the optical radiation and to direct it into the measurement cell; a detector, configured to measure wavelength dependent intensity values of the directed optical radiation after its interaction with the liquid; and a data processor coupled to receive the measured wavelength dependent intensity values and apply thereto a chemometric model linking wavelength dependent intensity values to components of the liquid sample. The optical analyser typically also comprises a liquid flow system having a flow conduit configured in serial flow communication with the measurement cell and provided with a first end for insertion into a liquid sample; and various valving and pumping elements, operable to transport liquid from the first end and into the measurement cell; and a controller for controlling the various valving and pumping elements located in fluid communication with the flow conduit to control the flow of liquid within the fluid conduit.

Making such optical spectroscopy measurements on liquids containing a dissolved gas, such as beers, is problematic since spontaneous expulsion of dissolved gas from liquid in the measurement cell may cause gas bubbles to be formed in the liquid. These gas bubbles act as "pin-holes" in the liquid, through which pin-holes the interrogating optical radiation may pass without interacting with the liquid. These pin-holes therefore adversely affect the measurements and reduce the reliability of the results.

Optical analysers for beers exist which address this problem in different ways.

One such known optical analyser for beers is configured to perform the optical spectroscopy measurement on liquid in a pressurised sealed container, such as in an unopened consumer container. The gas is thereby maintained in the liquid in a dissolved state to thereby inhibit bubble formation. However, measurements can only be made using containers that are transparent to the interrogating optical radiation.

Another such known optical analyser for beers is configured to perform the optical spectroscopy measurement on a liquid containing dissolved gas previously held in a sealed pressurised container. The liquid is first allowed to degas before the degassed liquid is transported via a liquid flow system to a measurement cell where measurement is made on an essentially gas-free liquid. Waiting for liquid to degas adds significantly to the analysis time of the sample, whereas mechanical agitation of the liquid to speed up degassing adds complexity and cost to the optical analyser or requires manual intervention.

A further such known optical analyser for beers is configured to perform the optical spectroscopy measurement on liquid previously held in a pressurised sealed container from which it is extracted into a liquid flow system of the analyser. The flow system is configured to maintain the extracted liquid at a pressure around or slightly above the pressure in the container. The gas therefore remains dissolved in the liquid during the optical spectroscopy measurement. However, such a liquid analyser requires a dedicated pressurising sub-system which is connected to the liquid flow system. This adds to the complexity and to the cost of the analyser.

SUMMARY

According to a first aspect of the present invention there is provided a method of performing an optical analysis of a liquid containing dissolved gas, such as beer, other potable liquid containing dissolved gas, or intermediate products in the manufacture of such potable liquids, the method comprising the steps of: transferring an amount of the liquid containing dissolved gas from a reservoir into a holder of a flow system of an optical analyser; holding the amount of the liquid containing the dissolved gas in the holder at around ambient pressure for a period selected to allow expulsion of a portion of dissolved gas from the amount of liquid; transferring at least a portion of the amount of the liquid containing the dissolved gas held in the holder under a pressure above ambient into a measurement cell of the optical analyser as a liquid sample; and performing an optical analysis of the liquid sample from a detection of optical radiation by an optical detector after its interaction with the liquid sample in the measurement cell. Thus time is saved by not having to wait for a total degassing and there are less requirements on the measurement system than would be necessary with using a higher pressure measurement cell and associated flow system when analysing a non-degassed sample. Moreover, there is no need for manual handling of the liquid in order to speed up complete degassing.

In some embodiments the flow system includes a piston pump configured such that its cylinder provides the holder and movement of its piston effects the transfers into and out of the holder. This simplifies the construction the optical analyser.

Usefully the holder may be vertically orientated. In this orientation gravity helps move the expelled dissolved gas into a layer above (in the direction of gravity) the liquid from which it has been expelled.

In some embodiments the step of transferring an amount of liquid from the reservoir comprises the steps of operating the piston of the piston pump to effect a first expansion stroke whereby an amount of the liquid containing dissolved gas is transferred from the reservoir into the cylinder; holding the amount of the liquid containing the dissolved gas in the cylinder at around ambient pressure; operating the piston to effect a compression stroke whereby a portion of the contents of the cylinder is transferred out of the cylinder, bypassing the measurement cell; and operating the piston to effect a further expansion stroke whereby an additional amount of the liquid containing dissolved gas is transferred from the reservoir into the cylinder, the additional amount being less than or equal to the portion. The amount of liquid containing dissolved gas relative to the amount expelled dissolved gas held in the cylinder is thereby increased.

In further embodiments the steps of holding the amount of the liquid containing the dissolved gas in the cylinder at around ambient pressure; operating the piston to effect a compression stroke whereby a portion of the contents of the cylinder is transferred out of the cylinder, bypassing the measurement cell; and operating the piston to effect a further expansion stroke whereby an additional amount of the liquid containing dissolved gas is transferred from the reservoir into the cylinder, the additional amount being less than or equal to the portion; are repeated at least once using compression and expansion strokes that are smaller than those employed in the immediately preceding repetition. This provides a further increase in the amount of liquid relative to expelled gas held in the cylinder and may permit the use of a smaller piston pump.

According to a second aspect of the present invention there is provided an optical analyser for beers comprising a measurement cell for receiving a beer sample, the measurement cell having a transparent wall section configured to permit transmission of optical radiation into the beer sample; an optical radiation source configured to generate the optical radiation; a complimentary optical radiation detector configured to detect the optical radiation after its interaction with the beer sample; a liquid flow system having a flow conduit configured in serial flow communication with the measurement cell and provided with an end for insertion into a reservoir containing beer; a piston pump disposed in serial fluid communication with a flow conduit at a location between the end and the measurement cell and a back pressure valve disposed in the flow conduit to generate a back pressure in the measurement cell; and a controller adapted to control the operation of the analyser to perform an optical analysis of the beer sample according to the method of the first aspect of the present invention.

BRIEF DESCRIPTION OF THE DRAWINGS

The above, as well as additional objects, features and advantages of the present invention, will be better understood through the following illustrative and non-limiting detailed description of embodiments of the present invention, made with reference to the appended drawings, of which.

DETAILED DESCRIPTION

In the following embodiments of the present invention will be described with respect to the analysis of beer or a beer intermediate product such as wort (collectively referred to herein as 'beer'). However it is intended that the invention is not limited to this application and, as will be appreciated by the skilled person, the present invention may be used for the analysis of any other liquid which contains a dissolved gas. Such liquids are typically potable liquids such as sparkling wines, carbonated soft drinks and waters, and their intermediate products.

Figure 1:
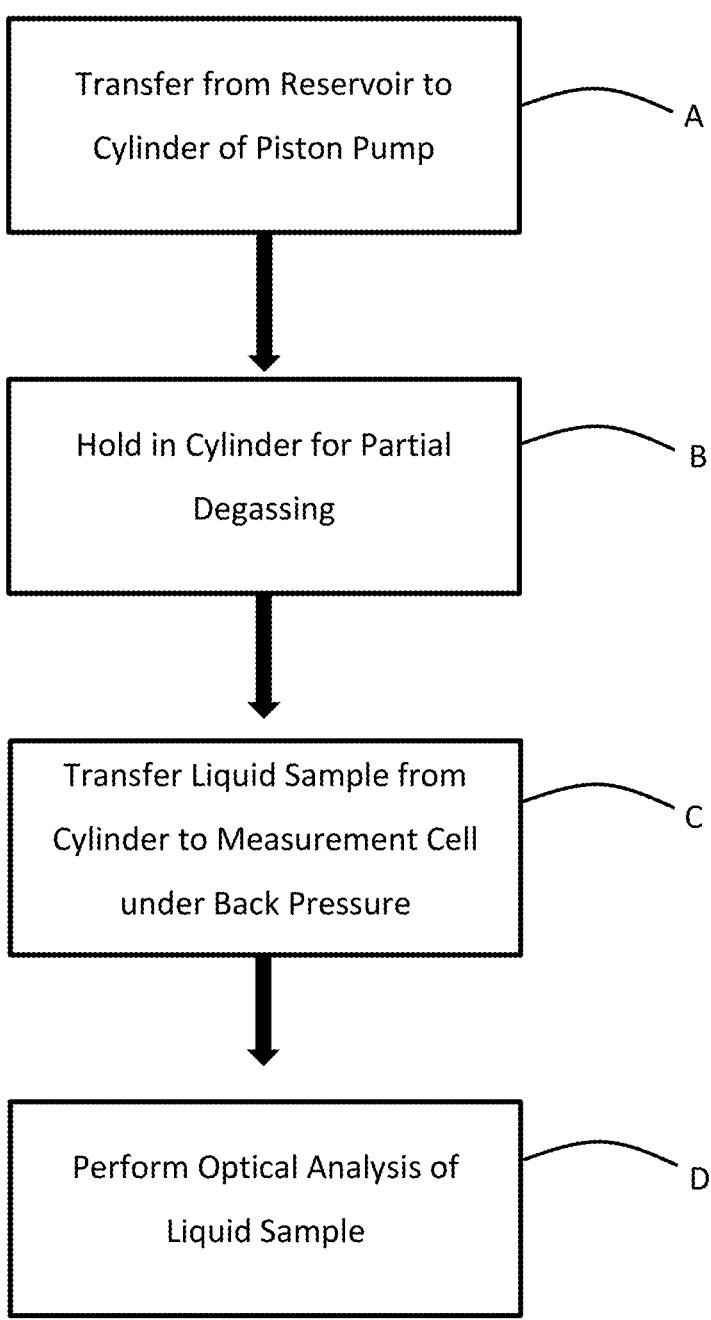
FIG. 1 is a flow chart illustrating an embodiment of the method according to the first aspect of the present invention.

A method of performing an optical analysis of beer is described in the flow chart which is illustrated in FIG. 1. At a first step A, a piston of a preferably vertically orientated piston pump which has its inlet connected in flow communication with a reservoir containing beer (or in other embodiments another liquid containing dissolved gas) is operated to transfer an amount of the beer from the reservoir into a cylinder of the preferably vertically orientated piston pump. In some embodiments transfer into the piston pump is done at a speed empirically determined to minimise or at least reduce degassing in the cylinder due to agitation of the liquid during transfer. At a second step B the amount of transferred beer is held in the preferably vertically orientated cylinder at or close to ambient pressure in order to permit partial degassing of the beer, in some embodiments for an equilibrium to establish between dissolved and expelled gas. The time that the beer needs to be held depends, in part, on the amount of gas dissolved in the beer in the reservoir, and may be determined empirically for each of a number of different beers or in some embodiments may be established using a single beer type known to have a high or maximum dissolved gas content. At a step C the piston is operated to transfer at least a portion of the beer from the cylinder under a pressure above ambient to provide a pressurised beer sample into a measurement cell of an optical analyser which is located in flow communication with the measurement cell. Being pressurised, development of bubbles in the beer sample during analysis will be inhibited. At a step D an optical analysis of the beer sample is made in a known manner from a detection of optical radiation by an optical spectrometer after its interaction with the liquid sample in the measurement cell.

Figure 2:
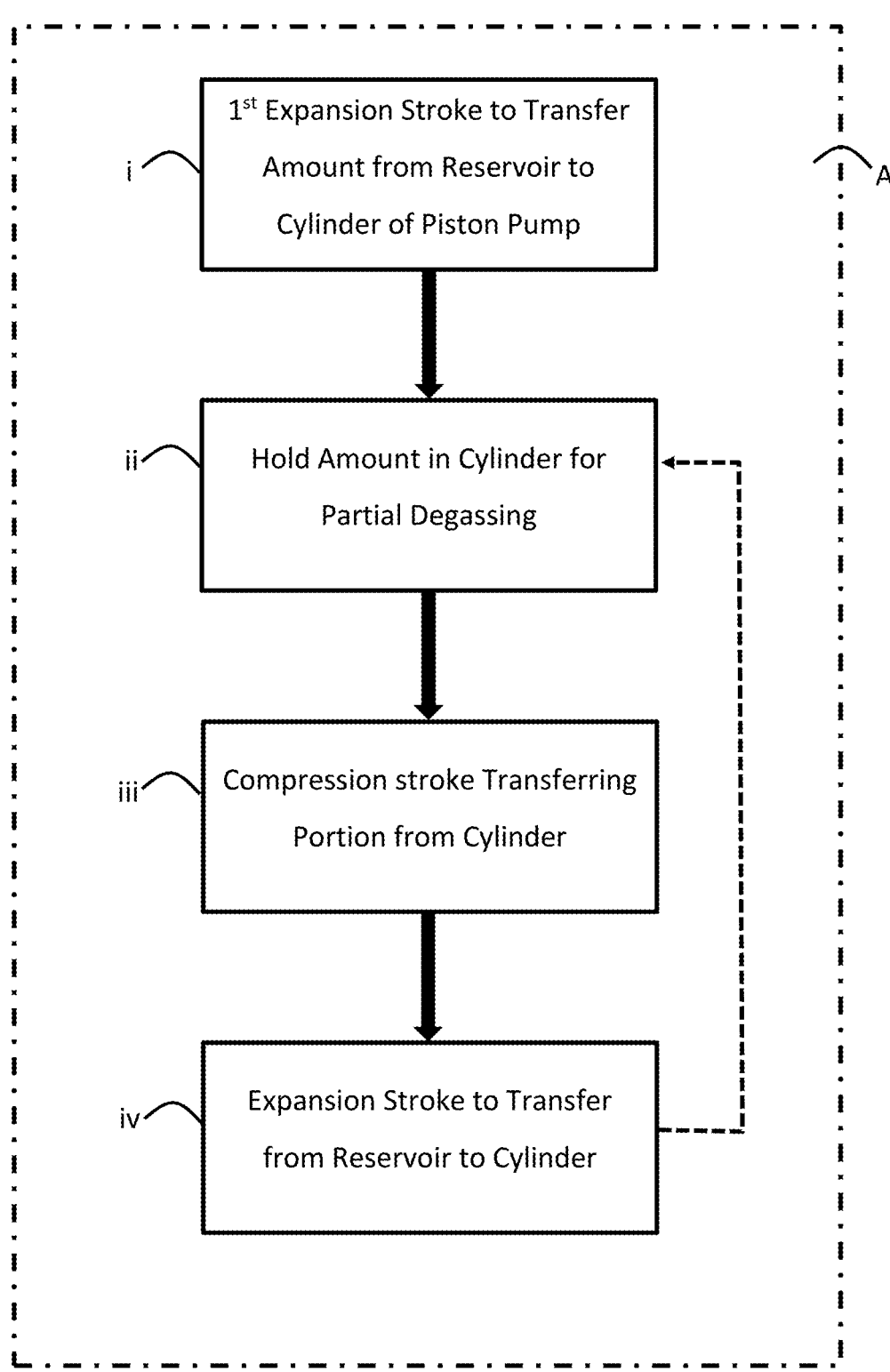
FIG. 2 is a flow chart illustrating steps of a further embodiment of the method of the present invention.

With reference to FIG. 2, in some embodiments the step A of transferring beer from the reservoir into the cylinder of the preferably vertically orientated piston pump comprises the steps of i) operating the piston to effect a first expansion stroke whereby an amount of the liquid containing dissolved gas is transferred from the reservoir into the cylinder; ii) holding the amount of the liquid containing the dissolved gas in the cylinder at around ambient pressure; iii) operating the piston to effect a compression stroke whereby a portion of the contents of the cylinder is transferred out of the cylinder, bypassing the measurement cell; and iv) operating the piston to effect a further expansion stroke whereby an additional amount of the liquid containing dissolved gas is transferred from the reservoir into the cylinder, the additional amount being less than or equal to the portion. This increases the amount of beer relative to the amount of expelled gas in the cylinder of the piston.

Usefully, the steps ii) to iv) may be repeated at least once with at each repetition the compression and expansion strokes performed at steps iii) and iv) respectively are made smaller than those employed in the immediately preceding steps ii) to iv). With each repetition, gas which has been expelled from the beer (typically retained above the beer as a foam) is removed from the cylinder and replaced with beer. This permits a smaller dimensioned piston pump to be employed since more of the contents of the cylinder will be beer available for transfer into the measurement cell at the step C of FIG. 1.

Figure 3:
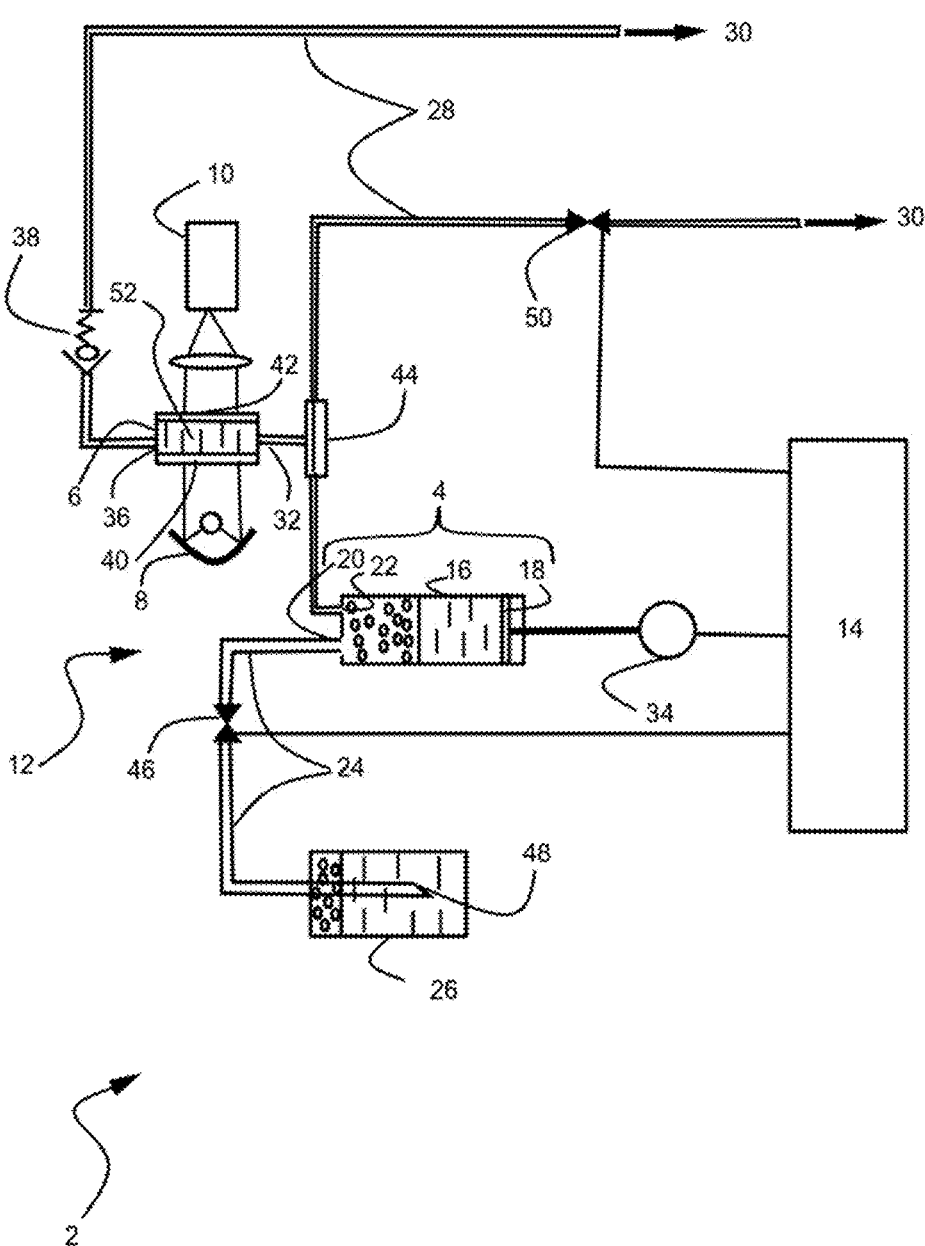
FIG. 3 is a schematic representation of an embodiment of optical analyser for beers according to the second aspect of the present invention.

FIG. 3 illustrates an embodiment of an optical analyser 2 according to a second aspect of the present invention adapted to perform the method according to the first aspect of the present invention, particularly with reference to the method illustrated in FIG. 1 and FIG. 2.

The optical analyser 2 comprises a vertically orientated piston pump 4; a measurement cell 6; an optical radiation source 8; a complementary optical radiation detector 10 for generating an output representative of a wavelength dependent intensity of incident optical radiation, such as is provided by a conventional interferometer or monochromator; a flow system 12 for transporting liquid within the analyser; and a controller 14, which may be one or more interconnected units that together operate to provide the functionality of the controller 14 as described in greater detail below.

The vertically orientated piston pump 4 comprises a vertically orientated cylinder 16 and a piston 18 which is reciprocally moveable within the vertically orientated cylinder 16 to effect expansion and compression strokes of the piston pump 4. A motor 34 is mechanically connected to the piston 18 and is operable to reciprocally move the piston 18. The vertically orientated cylinder 16 is provided with an inlet port 20 and an outlet port 22, which in some embodiments may be formed as a single port.

The inlet port 20 is connectable via a first flow conduit system 24 of the flow system 12 to a reservoir 26 containing, in use, a liquid containing dissolved gas to be analysed, here beer. The reservoir 26 may be, for example, a beaker or a consumer container such as a can or bottle. The outlet port 22 is connectable via a second flow conduit system 28 of the flow system 12 selectably to waste 30 or to an inlet 32 of the measurement cell 6. An in-line particle filter 44, such as a known cross-flow filter, is located in the second flow conduit system 28 to provide a filtered liquid sample to the inlet 32 of the measurement cell 6.

In the present embodiment separate inlet 20 and outlet 22 ports are provided. This enables the first flow conduit system 24 and the second flow conduit system 28 to be selected with different cross sectional areas. On the inlet side 20,24 of the piston pump 4 a low flow resistance is preferred, in order to avoid a low pressure which facilitates degassing of the liquid and foam generation in beer. On the outlet side 22,28 of the piston pump 4 a low volume is preferred.

The measurement cell 6 has on outlet 36 which is connected to waste 30 via a portion of the second flow conduit system 28 in which an in-line back-pressure valve 38 is located. The measurement cell 6 also has a transparent wall section, here formed as at least part of opposing walls 40, 42 of the measurement cell 6, through which optical radiation from the optical radiation source 8 can pass into liquid in the measurement cell 6 and through which light can pass to the complementary optical radiation detector 10 after its interaction with the liquid in the measurement cell 6. As is known in the art, in some embodiments the complementary optical radiation detector 10 may comprise a spectrometer, such as an interferometer or a monochromator, in other embodiments the optical radiation source 8 alternatively may include an interferometer or monochromator.

The flow system 12 also comprises controllable flow regulation, here provided by a first controllable on-off valve 46 located in the first flow conduit system 24 in-line between the inlet port 20 and an end 48 of a flow conduit of the first flow conduit system 24 which intended for introduction into the reservoir 26 and by a second controllable on-off valve 50 located in the second flow conduit system 28 in-line between the inlet 32 of the measurement cell and waste 30 and downstream of any in-line particle filter 44.

The controller 14 is connected at least to the motor 34 and to the first and the second controllable on-off valves 46,50 and is configured to generate control signals to control the operation of these elements 34,46,50 in order to have the optical analyser 2 perform the method according to the first aspect of the present invention.

In present embodiment the controller 14 thus operates in an intake phase (step A of FIG. 1) to generate signals closing the second on-off valve 50; opening the first on-off valve 46 and operating the motor 34 to move the piston 18 to effect an first expansion stroke (step i. of FIG. 2). In this first expansion stroke the piston 18 is moved a maximum stroke length in the cylinder 16 from a position proximal the inlet port 20 to a position distal of the inlet port 20 and thereby transfer a first amount of a liquid from the reservoir 26 and into the vertically orientated cylinder 16 of the piston pump 4. The controller 14 then generates signals to close the first on-off valve 46 and to open the second on-off valve 50. The first amount of liquid is held in the vertically orientated cylinder 16 at or around ambient pressure (step ii. of FIG. 2) for a predetermined period to allow the first amount of liquid to degas by a predetermined degree and separation of the contents of the cylinder 16 into a primarily gas containing phase (known as 'foam' in beer) above a primarily liquid phase containing dissolved gas. The controller then generates signals (step iii. of FIG. 2) to operate the motor 34 to move the piston 18 to effect a first compression stroke having a stroke length less than the stroke length of the first expansion stroke in order to transfer out of the cylinder 16 a first portion of its contents. This first portion will bypass the measurement cell due to the interactive effects of the in-line back-pressure valve 38 and the open second on-off valve 50 resulting in a lower pressure to waste 30. The controller 14 then generates signals (step iv. of FIG. 2) to close the second on-off valve 50; to open the first on-off valve 46; and to operate the motor 34 to move the piston 18 to effect a second expansion stroke having a stroke length less than or equal to the stroke length of the first compression stroke. In this manner, a second amount of liquid containing dissolved gas is transferred from the reservoir 26 and into the vertically orientated cylinder 16. In some embodiments the controller 14 may be adapted, through suitable programming say, to cycle sequentially through the generation of signals that correspond to the steps ii. to iv. described above, but with each cycle having smaller expansion and compression stroke lengths as compared to a preceding cycle, typically the immediately preceding cycle.

The controller then operates in a degas phase (step B of FIG. 1) to generate signals closing the first on-off valve 46 and opening the second on-off valve 50. The liquid in the cylinder 16 is thus held under ambient pressure for a predetermined time to permit a predetermined degree of degassing.

The controller 14 then operates in a transfer phase (step C. of FIG. 1) to generate signals to close the second on-off valve 50 and operate the motor 34 to effect a compression stroke of the piston 18 to transfer at least a portion of the (partially degassed) liquid containing dissolved liquid into the measurement cell 6 as a liquid sample 52. Transfer is made against a back pressure which is generated by the in-line back-pressure valve 38. This increases the pressure above the ambient pressure for the so transferred liquid sample 52 in the measurement cell 6 so that degassing is inhibited in the measurement cell 6. In some embodiments the transfer phase (step C. of Fig.) may comprise a first step in which a first part of the compression stroke is made with the second on-off valve 50 open. A portion of the contents of the cylinder 16, which is mainly gas/foam, is sent to waste 30, bypassing the measurement cell 6. A second step is then performed in which the second on-off valve 50 is closed, pressure is builds up in the cylinder 16 and a second part of the compression stroke is made by which liquid sample 52 enters the measurement cell 6 and will eventually flow through the in-line back-pressure valve 38 to waste 30 when its set back pressure is exceeded.

The controller 14 then operates in an analysis phase (step D. of FIG. 1) to generate signals to operate the optical radiation source 8 and the complementary optical radiation detector 10 to measure a wavelength dependent intensity of radiation from the optical radiation source 8 after its interaction with the liquid sample 52. As is well known in the art, an output of the complementary optical radiation detector 10 corresponding to this measurement, may then be subjected to a chemometric analysis in a data processor (not shown) in order to determine the presence and/or amount of one or more components of interest in the liquid sample 52.

The invention claimed is:

1. A method, the method comprising:
 A. transferring an amount of a liquid containing a dissolved gas from a reservoir into a holder of a flow system of an optical analyser, wherein the liquid transferred into the holder contains a first amount per unit of liquid volume of the dissolved gas;
 B. holding the amount of the liquid containing the dissolved gas in the holder at around ambient pressure based on the holder being open to a waste reservoir for a period of time such that a portion of the dissolved gas is expelled from the amount of the liquid held in the holder to reduce an amount of dissolved gas per unit of liquid volume in the amount of the liquid in the holder from the first amount per unit of liquid volume to a second amount per unit of liquid volume while the holder is open to the waste reservoir;
 C. transferring at least a portion of the amount of the liquid containing the second amount per unit of liquid volume of the dissolved gas held in the holder under an elevated pressure above ambient into a measurement cell of the optical analyser as a liquid sample, such that the liquid sample contains the second amount per unit of liquid volume of the dissolved gas; and
 D. performing an optical analysis of the liquid sample from a detection of optical radiation by an optical detector after interaction of the optical radiation with the liquid sample in the measurement cell while the liquid sample is at the elevated pressure above ambient within the measurement cell and contains the second amount per unit of liquid volume of the dissolved gas within the measurement cell.

2. The method according to claim 1 wherein the flow system comprises a piston pump having a piston moveable in a cylinder, the piston pump being arranged in the flow system to provide the cylinder as the holder.

3. The method according to claim 2 wherein step A. comprises:
 i. operating the piston to effect a first expansion stroke whereby an amount of the liquid containing dissolved gas is transferred from the reservoir into the cylinder;
 ii. holding the amount of the liquid containing the dissolved gas in the cylinder at around ambient pressure based on the holder being open to the waste reservoir;
 iii operating the piston to effect a compression stroke whereby a portion of contents of the cylinder is transferred out of the cylinder to the waste reservoir, bypassing the measurement cell; and
 iv. operating the piston to effect a further expansion stroke whereby an additional amount of the liquid containing dissolved gas is transferred from the reservoir into the cylinder, the additional amount being less than or equal to the portion of the contents of the cylinder.

4. The method according to claim 3, further comprising:
 repeating steps ii. to iv. at least once with compression and expansion strokes that are smaller than compression and expansion strokes employed in immediately preceding steps ii. to iv.

5. The method according to claim 1 wherein the liquid containing the dissolved gas is beer or a beer intermediate product.

6. The method according to claim 1, wherein the period of time is a predetermined period of time that is based on the liquid.

7. The method according to claim 6, wherein the period of time is empirically determined to be associated with a predetermined amount of expulsion of the dissolved gas from the amount of liquid held in the holder.

8. The method according to claim 6, wherein the period of time is associated with achieving an equilibrium between dissolved and expelled gas.

9. The method according to claim 1, wherein the transferring of at least the portion of the amount of the liquid containing the second amount per unit of liquid volume of the dissolved gas held in the holder under the elevated pressure above ambient includes
 transferring at least the portion of the amount of the liquid to the measurement cell against a back pressure generated by a back-pressure valve, the measurement cell in serial flow communication between the holder and the back-pressure valve, the back-pressure valve configured to open in response to a pressure exerted on the back-pressure valve by liquid transferred to the back-pressure valve through the measurement cell exceeding the back pressure, such that the elevated pressure above ambient equals the back pressure.

10. An optical analyser, the optical analyser comprising:
 a measurement cell configured to receive a liquid sample, the measurement cell having a transparent wall section configured to permit transmission of optical radiation into the liquid sample;
 an optical radiation source configured to generate the optical radiation;
 a complementary optical radiation detector configured to detect the optical radiation subsequent to interaction of the optical radiation with the liquid sample;
 a liquid flow system having a flow conduit configured in serial flow communication with the measurement cell and including an end configured to be inserted into a reservoir containing a liquid containing a dissolved gas;

a piston pump in serial fluid communication with the flow conduit at a location between the end and the measurement cell and an in-line back-pressure valve in the flow conduit, the in-line back-pressure valve configured to open in response to a pressure exerted on the in-line back-pressure valve by liquid transferred through the measurement cell exceeding a back pressure, the piston pump configured to generate the back pressure in the measurement cell based on causing liquid to be transferred against the in-line back-pressure valve through the measurement cell; and a controller that is configured to control an operation of the optical analyser to transfer an amount of the liquid containing the dissolved gas from the reservoir into a holder of the liquid flow system, wherein the liquid transferred into the holder contains a first amount per unit of liquid volume of the dissolved gas, hold the amount of the liquid containing the dissolved gas in the holder at around ambient pressure based on the holder being open to a waste reservoir for a period of time such that a portion of the dissolved gas is expelled from the amount of the liquid held in the holder to reduce an amount of dissolved gas per unit of liquid volume in the amount of the liquid in the holder from the first amount per unit of liquid volume to a second amount per unit of liquid volume while the holder is open to the waste reservoir, transfer at least a portion of the amount of the liquid containing the second amount per unit of liquid volume of the dissolved gas held in the holder under the back pressure above ambient into the measurement cell as the liquid sample, such that the liquid sample contains the second amount per unit of liquid volume of the dissolved gas, and perform an optical analysis of the liquid sample from a detection of the optical radiation by the complementary optical radiation detector after interaction of the optical radiation with the liquid sample in the measurement cell while the liquid sample is at the back pressure above ambient within the measurement cell and contains the second amount per unit of liquid volume of the dissolved gas within the measurement cell.

11. The optical analyser according to claim 10, wherein the piston pump is a vertically orientated piston pump.

12. The optical analyser according to claim 11, wherein the vertically orientated piston pump includes an inlet and an outlet that is separate from the inlet, the inlet being selectably connectable in liquid communication with the end of the flow conduit and the outlet selectably connectable in liquid communication with an inlet of the measurement cell.

13. The optical analyser according to claim 10, wherein the period of time is a predetermined period of time that is based on the liquid.

14. The optical analyser according to claim 13, wherein the period of time is empirically determined to be associated with a predetermined amount of expulsion of the dissolved gas from the amount of liquid held in the holder.

15. The optical analyser according to claim 13, wherein the period of time is associated with achieving an equilibrium between dissolved and expelled gas.

* * * * *